(12) United States Patent
Bäck (10) Patent No.: US 8,197,458 B2
(45) Date of Patent: Jun. 12, 2012

(54) SEAM JOINING TOGETHER AT LEAST TWO WEB MATERIALS

(75) Inventor: Lucas Bäck, Billdal (SE)

(73) Assignee: SCA Hygiene Products AB, Göteborg (SE)

( * ) Notice: Subject to any disclaimer, the term of this patent is extended or adjusted under 35 U.S.C. 154(b) by 387 days.

(21) Appl. No.: 12/307,964

(22) PCT Filed: Jul. 13, 2006

(86) PCT No.: PCT/SE2006/000858
§ 371 (c)(1),
(2), (4) Date: Jan. 8, 2009

(87) PCT Pub. No.: WO2008/008004
PCT Pub. Date: Jan. 17, 2008

(65) Prior Publication Data
US 2009/0292266 A1    Nov. 26, 2009

(51) Int. Cl.
*A61F 13/15* (2006.01)
*A61F 13/20* (2006.01)
*B41M 5/00* (2006.01)

(52) U.S. Cl. .................... 604/396; 428/195.1

(58) Field of Classification Search ............... 604/396; 428/195.1
See application file for complete search history.

(56) References Cited

U.S. PATENT DOCUMENTS

| | | | |
|---|---|---|---|
| 4,205,679 A | 6/1980 | Repke et al. | |
| 4,627,853 A | 12/1986 | Campbell et al. | |
| 4,916,005 A | 4/1990 | Lippert et al. | |
| 4,938,817 A | 7/1990 | Langley | |
| 4,964,860 A | 10/1990 | Gipson et al. | |
| 5,006,385 A | 4/1991 | Cheung et al. | |
| 5,226,992 A | 7/1993 | Morman | |
| 5,626,574 A * | 5/1997 | Sasaki et al. | 604/385.29 |
| 5,919,539 A | 7/1999 | Bisbis et al. | |
| 6,086,571 A | 7/2000 | Guevara et al. | |

(Continued)

FOREIGN PATENT DOCUMENTS

EP    0 287 338 A2    10/1988

(Continued)

OTHER PUBLICATIONS

Form PCT/ISA/210 (International Search Report) dated Feb. 22, 2007.

(Continued)

*Primary Examiner* — Melanie Hand
(74) *Attorney, Agent, or Firm* — Buchanan Ingersoll & Rooney PC (57) ABSTRACT

A seam joining together at least two web materials in an overlapped manner, wherein the overlapped portions are bonded together by ultrasonic welding, heat bonding, laser welding or the like, in a bonding pattern extending over at least a part of the overlapped portion to form said seam. The bonding pattern has a main bonding pattern extending in longitudinal direction along at least a part of the overlapped portion, and at least one edge bonding pattern extending in longitudinal direction along at least a part of along and adjacent at least one side edge of the overlapped portion, the bonded area of said edge bonding pattern occupying no more than 30% of the total bonded area of the central bonding pattern plus the bonded area of the edge bonding pattern. The seam may be present in a personal care absorbent article.

16 Claims, 6 Drawing Sheets

U.S. PATENT DOCUMENTS

| | | | |
|---|---|---|---|
| 6,245,051 | B1 | 6/2001 | Zenker et al. |
| 6,713,159 | B1 * | 3/2004 | Blenke et al. ............ 428/195.1 |
| 7,217,262 | B2 | 5/2007 | Nakahata et al. |
| 2001/0041879 | A1 | 11/2001 | Karami et al. |
| 2002/0188268 | A1 | 12/2002 | Kline et al. |
| 2003/0199841 | A1 * | 10/2003 | Ashton et al. ............ 604/385.01 |
| 2004/0017885 | A1 | 1/2004 | Antoni et al. |
| 2004/0116889 | A1 | 6/2004 | Carbone, II et al. |
| 2005/0131373 | A1 | 6/2005 | Wright et al. |
| 2006/0089616 | A1 | 4/2006 | Belau et al. |
| 2006/0149209 | A1 | 7/2006 | Malchow et al. |

FOREIGN PATENT DOCUMENTS

| | | |
|---|---|---|
| EP | 0 409 307 A2 | 1/1991 |
| EP | 0 487 758 A1 | 6/1992 |
| EP | 0 605 012 A1 | 7/1994 |
| EP | 0 646 062 B1 | 8/1996 |
| EP | 10 35 818 A1 | 9/2000 |
| EP | 1 077 054 A2 | 2/2001 |
| EP | 1 110 529 A1 | 6/2001 |
| EP | 1 216 612 | 6/2002 |
| EP | 1 236 456 A2 | 9/2002 |
| FR | 2 582 517 A1 | 12/1986 |
| FR | 2 586 558 A1 | 3/1987 |
| GB | 1 332 037 | 10/1973 |
| GB | 2 231 837 | 11/1990 |
| JP | 3471999 | 6/1997 |
| JP | 2008-522781 | 7/2008 |
| WO | WO 91/08725 A1 | 6/1991 |
| WO | WO 94/00292 A1 | 1/1994 |
| WO | WO 98/29251 A1 | 7/1998 |
| WO | WO 99/27876 A1 | 6/1999 |
| WO | WO 01/00129 A1 | 1/2001 |
| WO | WO 02/17843 | 3/2002 |
| WO | WO 02/32364 A1 | 4/2002 |
| WO | WO 03/000165 A1 | 1/2003 |
| WO | WO 03/047488 A1 | 6/2003 |
| WO | WO 2004/017885 A1 | 3/2004 |
| WO | WO 2006/065175 A1 | 7/2006 |

OTHER PUBLICATIONS

Form PCT/ISA/237 (Written Opinion of the International Searching Authority) dated Feb. 22, 2007.

U.S. Appl. No. 12/305,685, Lucas Back et al., "Belted Absorbent Garment", filed Dec. 19, 2008.

U.S. Appl. No. 12/305,701, Kent Hermansson, "Belted Absorbent Garment", filed Dec. 19, 2008.

Supplementary European Search Report dated Aug. 4, 2010, issued in the corresponding European Application No. 06758042.3-2307.

English translation of Notice of Reasons for Rejection issued May 31, 2011 in corresponding Jp 2009- 519400.

* cited by examiner

SEAM JOINING TOGETHER AT LEAST TWO WEB MATERIALS

PRIORITY

This application is a national stage application of PCT/SE2006/000858, filed 13 Jul. 2006.

TECHNICAL FIELD

The present disclosure refers to a seam joining together at least first and second web materials, at least one of which comprising heat fusible material, the first web material having a side edge overlapping with a side edge of the second web material, wherein an overlapped portion is formed where said web materials overlap. The web materials in said overlapped portion are bonded together by ultrasonic welding, heat bonding, laser welding or the like, in a bonding pattern extending over at least a part of the overlapped portion to form said seam.

BACKGROUND

Web materials comprising heat fusible material, either fibrous webs, films or laminates thereof, are used in a variety of applications, such as protective clothing and hygiene articles, especially disposable absorbent personal care articles, like diapers, sanitary napkins and incontinence guards. In most of such applications the web materials must be joined, which is conventionally done by ultrasonic welding, heat bonding, laser welding or by adhesive. Bonding by ultrasonic welding, heat bonding or laser welding is usually done by forming a bonding pattern comprising a plurality of bonding sites in which the heat fusible components of the web materials are fused and thus bonded together.

The bonding is done in a process line, in which material variations as well as process variations may occur, which can effect the exact positioning of the bonding pattern with respect to the overlapping side edges of the web materials. If the bonding pattern ends up being located a bit offset with respect to the overlap, an edge of the overlap may protrude from the surface of the joined web materials. This will reduce the quality of the seam and of the article and if used in an article worn against the skin of a wearer such a protruding edge may cause skin irritations.

U.S. Pat. No. 5,919,539 discloses ultrasonic seaming of spunbonded polyolefin sheets for example used in protective clothing. The overlapping sheet edges are fed between an ultrasonic horn and a patterned roll that has a raised pattern corresponding to the desired bonding pattern. A waffle-like bonding pattern is created and the edges of the sheet are welded over so as to eliminate protruding sheet edges along the seam.

U.S. Pat. No. 5,626,574 refers to a disposable diaper having a front and a back body panel bonded to each other by ultrasonic welding to form side seams. The welded side seams are defined by patterns of intermittently arranged bonding sites of different shape. The purpose is to create a welding pattern which allows the side seams to be torn open longitudinally along the welded zones.

U.S. Pat. No. 4,938,817 shows a welding pattern for joining two overlapping material webs, said welding pattern comprises short dashed lines extending in parallel to the edges of the fabric.

U.S. Pat. No. 4,205,679 discloses a disposable undergarment in which a strong ultrasonic weld seam is formed by a plurality of weld lines extending in longitudinal direction of the overlapping side edges spaced inwardly from the edges of the overlap.

There is a need for an improved bonding pattern for seams joining together at least two web materials of the above mentioned kind, said bonding pattern providing both a strong seam along the overlap and a reduced risk for protruding edges along the seam

OBJECT AND SUMMARY

The present disclosure aims at solving the problem set out above and suggests that said bonding pattern comprises a main bonding pattern extending in longitudinal direction along at least a part of the overlapped portion, and at least one edge bonding pattern extending in longitudinal direction along and adjacent at least a part of at least one of said side edges, the bonded area of said edge bonding pattern(s) occupying no more than 30% of the total bonded area of the main bonding pattern plus the bonded area of the edge bonding pattern(s).

This means that the area occupied by bonding sites in the edge bonding pattern(s) should be no more than 30% of the total area occupied by bonding sites in the edge bonding pattern(s) plus the main bonding pattern.

The main bonding pattern provides for a strong seam along the overlap, while the edge bonding pattern bonds down the side edges along the overlap. Due to the limited bonding area of the side edge bonding pattern the softness and flexibility in this region of the seam is substantially maintained.

In one embodiment said edge bonding pattern occupies at least 5%, preferably at least 7% of the total bonding area occupied by the combined central bonding pattern and edge bonding pattern.

In a further aspect said edge bonding pattern occupying no more than 25% of the total bonding area occupied by the combined central bonding pattern and edge bonding pattern.

The edge bonding pattern may be in the form of a plurality of small bonding sites each having an area of no more than 4 $mm^2$.

The central bonding pattern is defined in longitudinal direction, y, by an outer limiting margin and the edge bonding pattern is defined in longitudinal direction, y, by an inner limiting margin, wherein in one embodiment the distance between said outer and said inner limiting margin is at least 1.5 mm.

According to one embodiment said bonding pattern comprises two edge bonding patterns, one on each side of the central bonding pattern.

The distance between the inner limiting margins of the two edge bonding patterns is in one embodiment between 25 and 95%, preferably between 30 and 80% of the width of the seam in transverse direction, x.

The width of the seam in transverse direction, x, is in according to one aspect of the disclosure between 8 and 30 mm.

The main central bonding pattern has according to one embodiment a bonding density of between 10 and 80%, preferably between 20 and 60%. The edge bonding pattern has according to a further embodiment a bonding density of at least 2% and no more than 60%, preferably no more than 50% and more preferably no more than 30%.

"Bonding density" is herein defined as the area occupied by bonding sites in relation to the entire area circumscribed by the bonding pattern including the non-bonded areas between bonding sites.

In one aspect of the disclosure the web materials have a basis weight between 25 and 130 g/m².

In a further aspect of the disclosure at least one of the web materials is an elastic material.

In a still further aspect the seam is present in a personal care absorbent article comprising an absorbent structure and first and second web materials comprising heat fusible material joined together to form said seam.

The personal care absorbent article is in one embodiment a pant-like garment comprising a first body panel, a second body panel and a crotch portion there between, said first and second body panels being joined together in an overlapped manner by a bonding pattern as described to form side connections forming said seam.

In a further embodiment the personal care absorbent article is a pant-like garment comprising a first body panel, a second body panel and a crotch portion there between, said first and second body panels being joined together to form side connections and further being provided with an elastic waistband, said waistband being joined to the first and/or second body panels in an overlapped manner by a bonding pattern as described to form said seam.

In a still further embodiment the personal care absorbent article is an absorbent garment such as a diaper and an incontinence guard comprising a first body panel, a second body panel and a crotch portion there between, each of said first and second body panels having a waist portion, said garment further being provided with opposed laterally extending belt members attached to the waist portion of the first body panel and being adapted to be wrapped around the waist of the wearer of the garment and fastened together by means of first fastening means, the second body panel at its waist portion being provided with second fastening means adapted to be fastened to the belt members, in such a way that the garment will assume a pant-like shape, said belt members being joined to first body panel in an overlapped manner by a bonding pattern as described to form said seam.

BRIEF DESCRIPTION OF THE DRAWINGS

The disclosure will in the following be closer described with reference to some embodiments shown in the accompanying drawings. It should be further understood that the drawings are not necessarily drawn to scale and that, unless otherwise indicated, they are merely intended to conceptually illustrate the structures described herein.

DESCRIPTION OF PREFERRED EMBODIMENTS

Figure 1A:
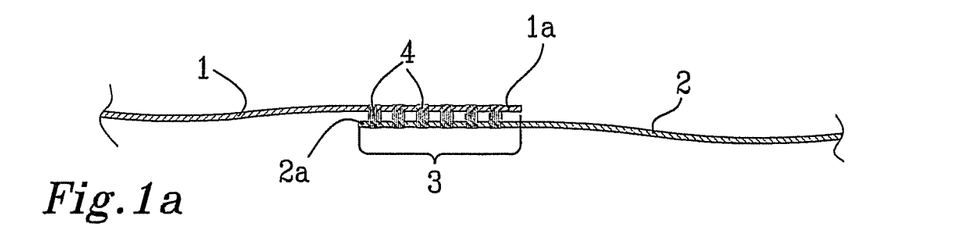
FIG. 1a shows a schematic side view of a welded seam between two overlapping web materials.
Figure 1B:
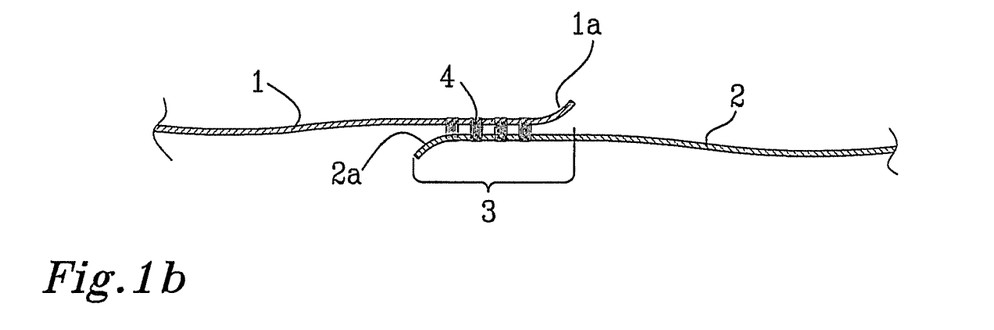
FIG. 1b is a corresponding view showing a bonding pattern which is narrower than the overlap between the webs.

FIGS. 1a and b illustrate schematically two overlapping web materials 1 and 2 at least one of which comprising heat fusible material. The webs may be a fibrous nonwoven material, a plastic film or laminates thereof. The overlapped portion between the two webs is denoted with the numeral 3. The webs 1 and 2 are in the overlapped portion joined by a bonding pattern 4 comprising a plurality of bonding sites. The bonding is accomplished by any method known in art in which the heat fusible material is caused to melt and thus bond the webs 1 and 2 together, for example ultrasonic welding, heat bonding, laser welding or the like. The thus bonded overlapped portion forms a seam joining together the two web materials 1 and 2. The seam is located in the same plane as the two web materials. Both webs have portions extending outside the overlap.

In FIG. 1a the overlapped portion 3 is rather narrow and the bonding pattern 4 extends over the entire width of the overlapped portion. Thus the respective side edges 1a and 2a of the two web materials are located close to the edges of the bonding pattern 4. This is an appealing look for a seam, but difficult to achieve in a process line running at high speeds.

It is favourable to have both web materials 1 and 2 covering the entire bonding pattern 4. If the bonding pattern 4 extends outside the overlapped portion 3, no bonding will occur in this region which means that the bonding area gets smaller and the energy level increases in the actual bonding area, which may cause burn through of the material.

FIG. 1b shows an overlapped portion 3 that is wider than the width of the bonding pattern 4. Thus the edges 1a and 2a of the web materials extend beyond the edges of the bonding pattern. This is easier to achieve in a process line, but not as appealing as the seam in FIG. 1a, since the web material side edges 1a and 2a will protrude from the plane of the web materials.

Figure 2A:
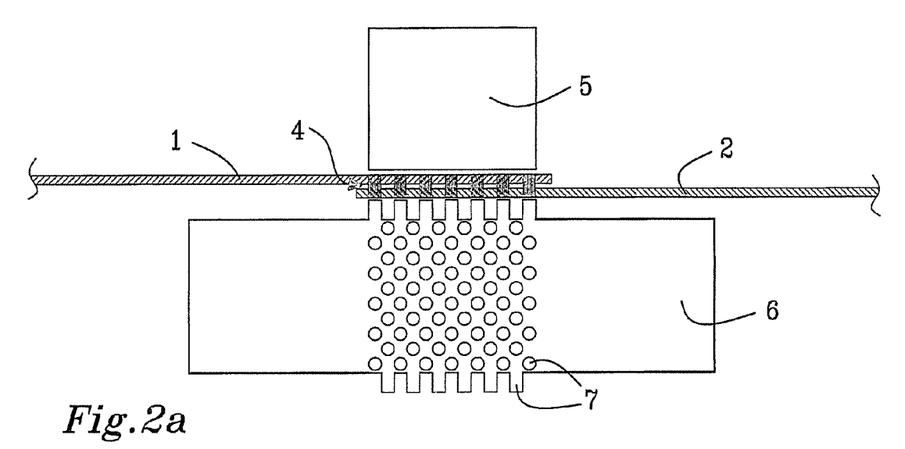
FIG. 2a shows a schematic side view of an ultrasonic welding equipment generating a weld seam between two overlapping web materials.
Figure 2B:
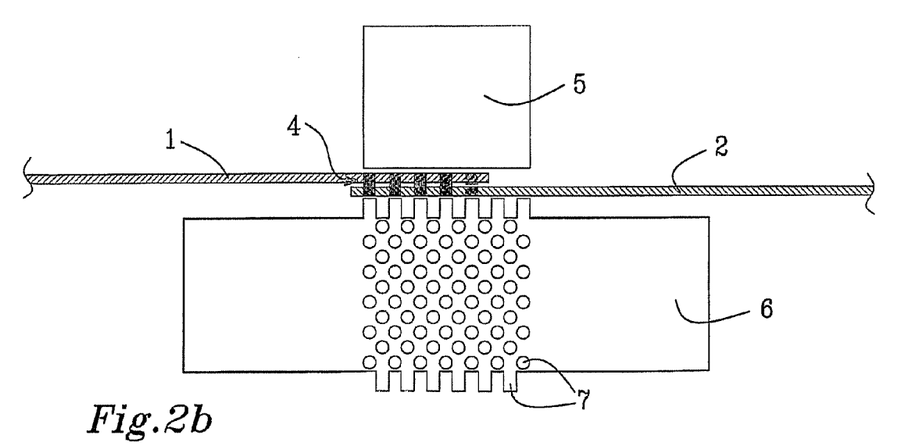
FIG. 2b is a corresponding view showing the ultrasonic equipment located a bit offset with respect to the overlap between the web materials.

FIGS. 2a and 2b are schematic side views of an ultrasonic welding equipment comprising an ultrasonic horn 5 and an anvil roll 6 with a pattern of protuberances 7 for generating the bonding pattern. A pair of overlapping web materials 1 and 2 passes in the gap between the ultrasonic horn 5 and the anvil roll 6 to be ultrasonically welded together. The ultrasonic energy causes the portions of the web materials that are pressed against the horn 5 to momentarily melt and thus bond the web materials together in the area where the protuberances 7 on the anvil roll 6 presses the material against the horn 5. If, as shown in FIG. 2b, the pattern of protuberances 7 generating the bonding pattern extend outside the overlapped portion of the two web materials the bonding area decreases resulting in an increase of ultrasonic energy per unit bonding area. As discussed above this may result in burn through of the web materials.

Thus there is a problem to achieve a high quality seam between web materials in a process line running at high speed and in which small variations in the width of the overlapped portions and/or the exact location thereof may occur.

The present disclosure aims at suggesting a bonding pattern which is less sensitive to such process variations and which provides a high quality seam even if the bonding pattern may end up slightly offset with respect to the overlapped portions of the web materials.

Figure 3A:
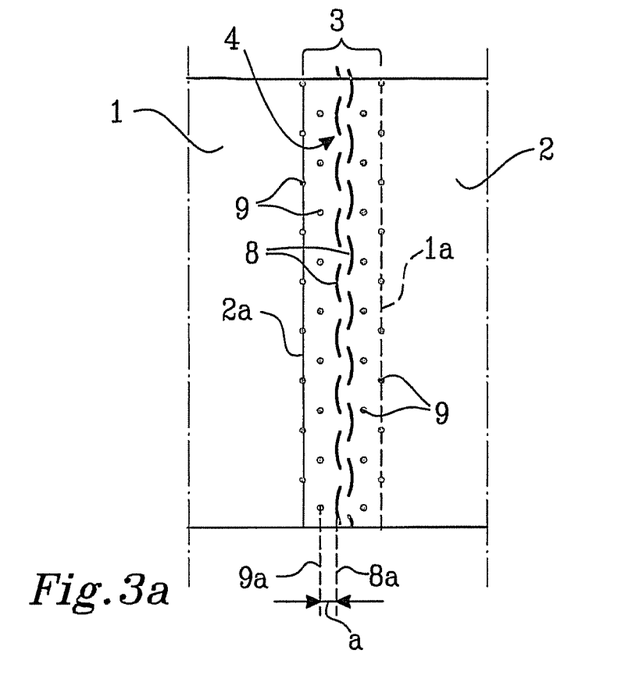
FIG. 3a is a plan view of two overlapping web materials bonded with a bonding pattern according to an embodiment of the disclosure.
Figure 3B:
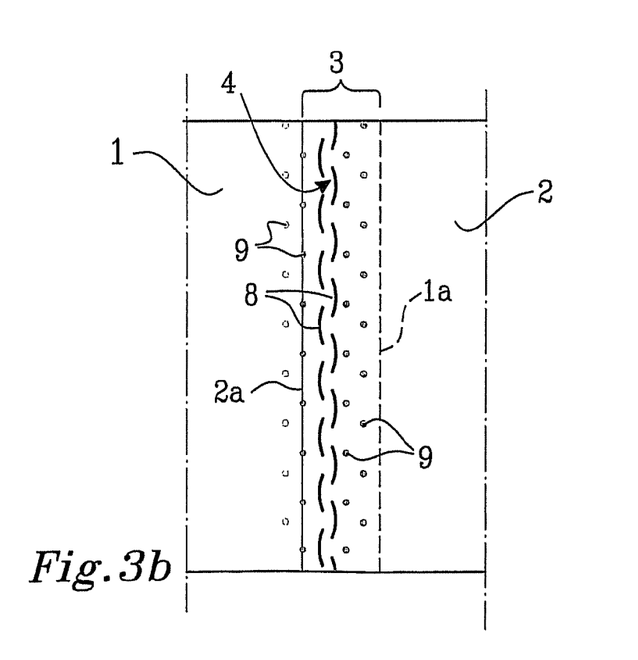
FIG. 3b is a corresponding view but showing the bonding pattern a bit offset with respect to the overlap.

An example of a bonding pattern according to the disclosure is shown in FIGS. 3a and b. The bonding pattern 4 comprises a main bonding pattern 8 extending in longitudinal direction, y, centrally along the overlapped portions 3 and edge bonding patterns 9 extending in longitudinal direction along both sides of the main bonding pattern 8 adjacent the respective side edge 1a and 2a of the web materials. In an alternative embodiment only one edge bonding pattern 9 is provided, in which case the main bonding pattern 8 may be located offset with respect to the longitudinal center of the overlapped portion 3, closer to the opposite side edge having no edge bonding pattern 9.

The main bonding pattern 8 occupies a larger bonding area than the edge bonding pattern(s) 9, such that the edge bonding pattern(s) 9 occupy no more than 30%, preferably no more than 25% of the total bonding area occupied by the combined main bonding pattern 8 and edge bonding patterns 9. As mentioned above this means that the area occupied by bonding sites in the edge bonding pattern(s) 9 should be no more than 30% of the total area occupied by bonding sites in the edge bonding pattern(s) 9 plus the main bonding pattern.

In case of two edge bonding patterns, one on each side of the main bonding pattern, it is further preferred that the edge bonding patterns occupy at least 5%, preferably at least 7% of the total bonding area occupied by the combined central bonding pattern and edge bonding patterns. If only one edge bonding pattern is provided it is preferred that the edge bonding pattern occupies between 2 and 20% of the total bonding area occupied by the combined central bonding pattern and edge bonding pattern.

The main bonding pattern 8 has longitudinal outer limiting margins 8a on either sides, said margins 8a being tangents to the main bonding pattern along its opposite sides. The respective edge bonding pattern 9 has a longitudinal inner limiting margin 9a, said margin being a tangent to the edge bonding pattern 9 along the side thereof facing the main bonding pattern 8. The distance between the outer limiting margin 8a of the main bonding pattern 8 and the respective edge bonding pattern 9 is in FIG. 3a denoted with a. The distance a is preferably at least 1.5 mm.

The distance between the inner limiting margins 9a of the two edge bonding patterns is preferably between 25 and 95%, preferably between 30 and 80% of the width of the overlapped portion 3 in transverse direction, x.

The main bonding pattern 8 has preferably a bonding density of between 10 and 80%, preferably between 20 and 60%, while the edge bonding patterns have a bonding density of at least 2% and no more than 60%, preferably no more than 50% and more preferably no more than 30%.

The bonding density is defined as the area occupied by bonding sites in relation to the entire area circumscribed by the bonding pattern including the non-bonded areas between bonding sites.

Figure 4A:
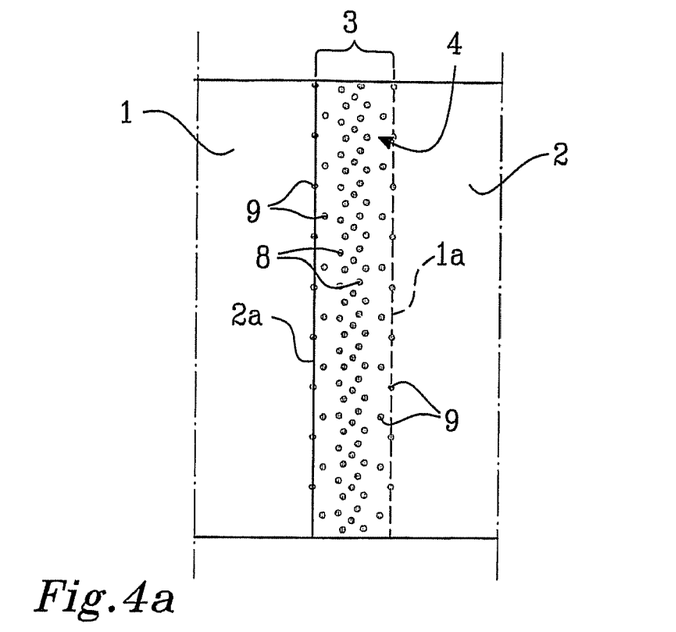
FIGS. 4a and b are plan view of two overlapping web materials bonded with alternative bonding patterns.
Figure 4B:
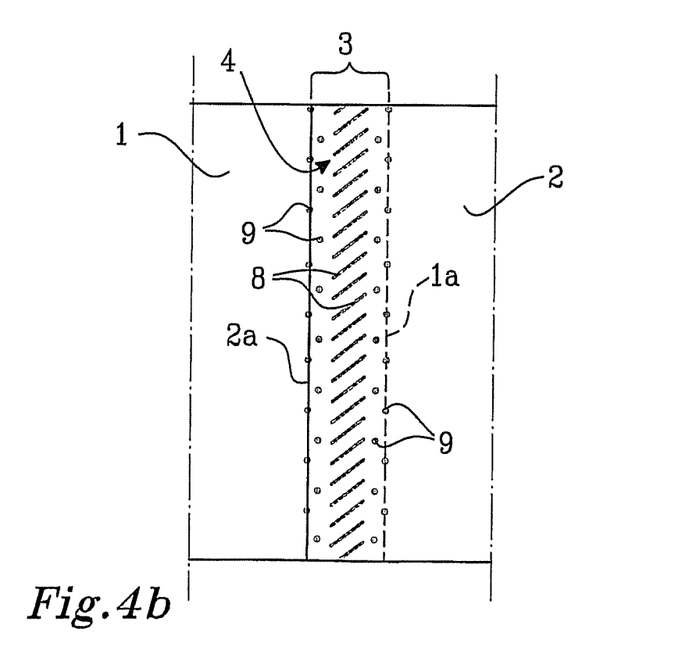

FIGS. 4a and b show examples of alternative bonding patterns according to the disclosure.

The edge bonding pattern 9 is preferably in the form of a plurality of small bonding sites, such as dot, lines or the like, each having an area of no more than 4 mm$^2$. The main bonding pattern 8 may comprise larger bonding sites or alternatively a plurality of small bonding sites, located denser than the bonding sites of the edge bonding patterns 9.

The main bonding pattern 8 provides for a strong seam along the overlapped portion 3, while the edge bonding patterns 9 bond down the side edges 1a, 2a which extend laterally beyond the edges of the main bonding pattern. Due to the limited bonding area of the side edge bonding pattern the softness and flexibility in this region of the seam is substantially maintained.

In FIG. 3b it is shown a bonding pattern 4 located slightly offset with respect to the overlapped portion 3. The main bonding pattern 8 is however located within the overlapped portion and only part of one edge bonding pattern 9 has ended up laterally outside the overlapped portion. The quality of the seam will still be high since the minor part of the bonding pattern located outside the overlapped portion 3 will decrease the bonding area only to a minor extent, thus resulting in only a minor increase of the ultrasonic energy per unit bonding area.

The width of the bonding pattern in transverse direction, x, can be made substantially equal to or only slightly smaller than the width of the overlapped portion 3 in transverse direction. This means that it is prevented that the side edges 1a and 2a of the web materials 1 and 2 protrude from the plane of the web materials, but are bonded down by the edge bonding patterns 9.

The bonding pattern according to the disclosure is less sensitive than traditional bonding patterns to process variations which may cause the bonding pattern to end up slightly offset with respect to the longitudinal center of the overlapped portion 3.

The disclosure is especially applicable on web material having a basis weight between 25 and 130 g/m$^2$. At least one web material is in one embodiment of the disclosure an elastic material, such as an elastic film, an elastic nonwoven or an elastic laminate therefrom. An elastic material is defined as a material having an elasticity of at least 30% in the elasticity test described below.

The width of the overlapped portion 3 in transverse direction, x, is preferably between 8 and 30 mm.

Figure 6:
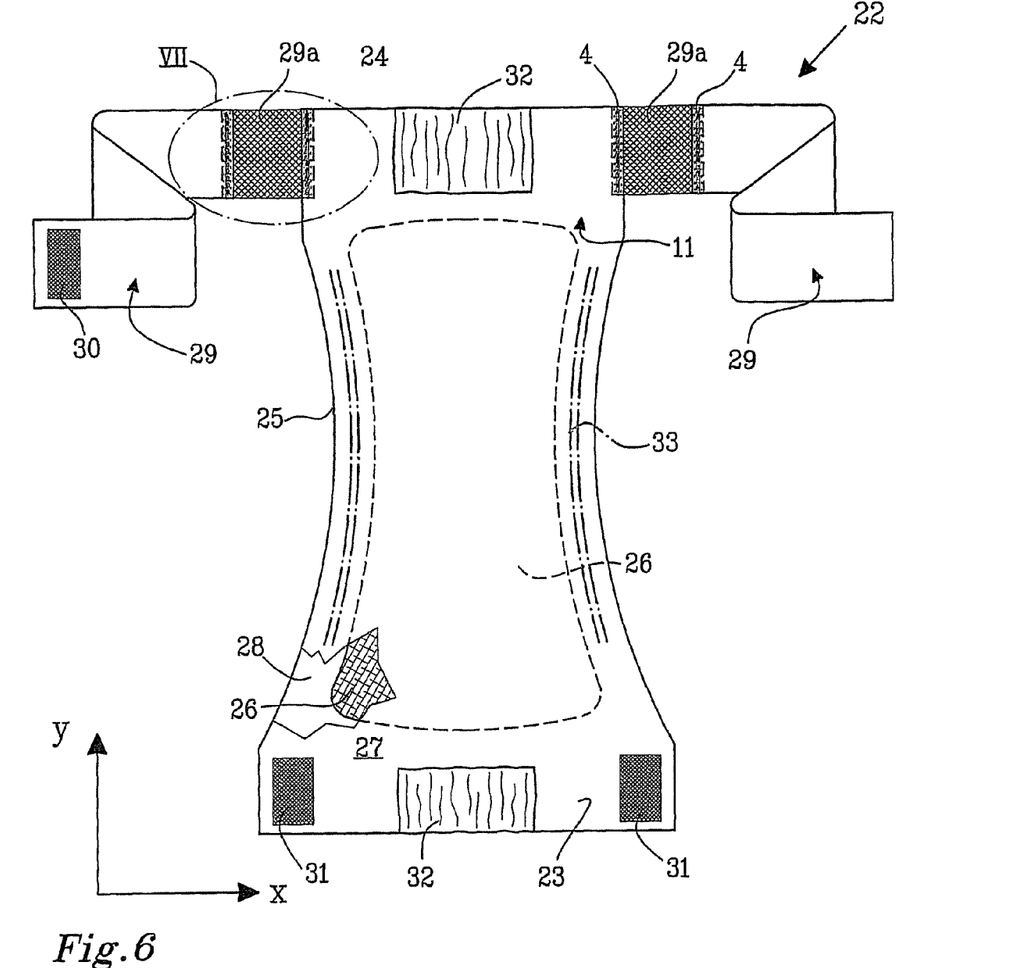
FIG. 6 is a plan view of a belted diaper.
Figure 7:
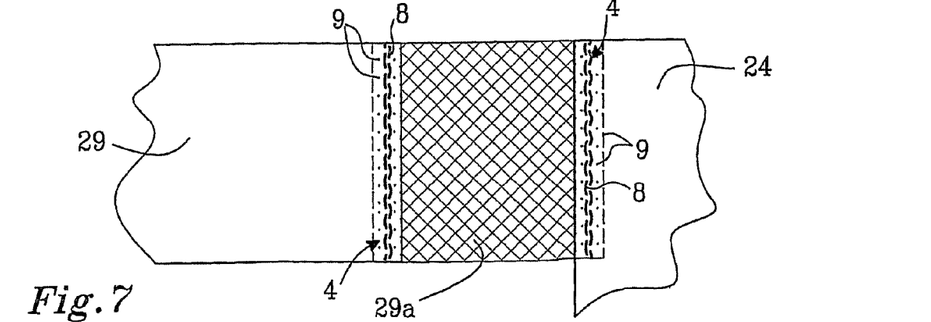
FIG. 7 shows on a larger scale a detail from FIG. 6, namely the attachment of the belt to the article.

One important application of the disclosure is in personal care absorbent articles such as diapers, incontinence guards, sanitary napkins and the like comprising an absorbent structure and web materials joined together to form different components of the articles. Examples of seams in absorbent articles which may use the bonding pattern according to the disclosure are shown in FIGS. 5-7.

Figure 5:
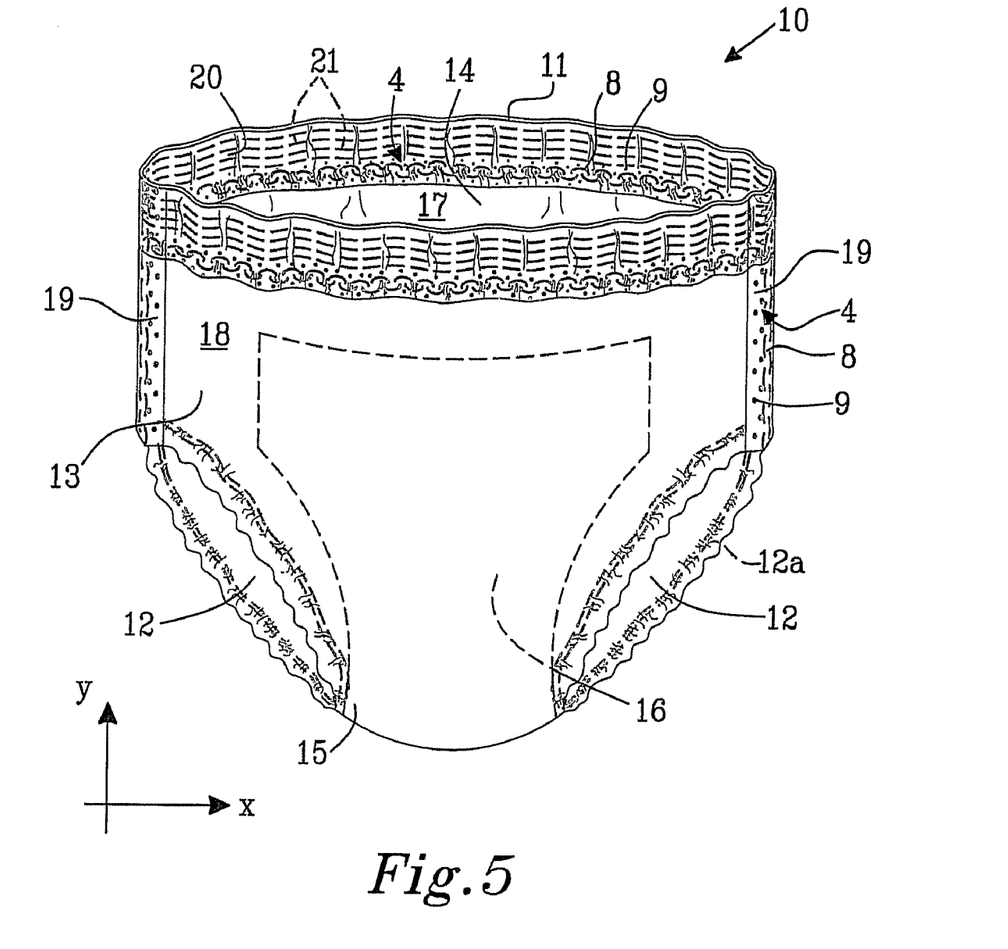
FIG. 5 is a perspective view of a pant-type absorbent article.

FIG. 5 shows a pant-type absorbent article 10 having a defined waist opening 11 and a pair of leg openings 12 and which are pulled onto the body of the wearer by inserting the legs into the leg openings and pulling the article up over the waist. Examples of such pant-type absorbent article are pant diapers, training pants, swim pants, sanitary pants and incontinence pants worn by incontinent adults. The article will in the following be referred to as a "pant diaper". The article has a longitudinal direction y and a transverse direction x.

The pant diaper comprises a front body panel 13, which is the part of the pant diaper that in use is intended to extend over the stomach and front hip area of the wearer. The article also comprises a back body panel 14, which is the part of the article that in use is intended to extend over the back and the rear hip area of the wearer. The crotch portion 15 of a pant diaper article is the part of the diaper that in use is intended to extend through the wearer's crotch area, between the legs.

An absorbent core 16 is disposed in the crotch portion 15 and extends into the front and back body panels 13 and 14. The absorbent core is disposed between an inner coversheet 17 and an outer coversheet 18.

The term "inner coversheet" refers to the liquid permeable material sheet forming the inner cover of the absorbent article and which in use is placed in direct contact with the skin of the wearer. The inner coversheet can comprise a nonwoven material, e.g. spunbond, meltblown, carded, hydroentangled, wetlaid etc. Suitable nonwoven materials can be composed of natural fibers, such as woodpulp or cotton fibres, man-made fibres, such as polyester, polyethylene, polypropylene, viscose, rayon etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent article.

The "outer coversheet" refers to the material forming the outer cover of the absorbent article. The outer coversheet may be the same or different in different parts of the absorbent article. At least in the area of the absorbent core the outer coversheet comprises a liquid impervious material a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet comprises a nonwoven material on at least the garment-facing surface thereof.

The "absorbent core" is the absorbent structure disposed between the two coversheets of the absorbent article in at least the crotch region thereof. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

A high liquid storage capacity is provided by the use of high amounts of superabsorbent material. For an absorbent core comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

The front and back body panels 13 and 14 or those parts thereof that are located outside the absorbent core region may have different material composition than the crotch portion 15. Thus according to one embodiment the areas of the front and back body panels 13 and 14 which are located outside the absorbent core region may be composed of for example a laminate material having a body facing side and a garment facing side, while a liquid impervious outer coversheet and/or a liquid pervious inner coversheet only is present in the absorbent core region. In other embodiments the inner and outer coversheets are the same in the front and back body panels 13 and 14 as well as in the crotch region 15.

The entire or part of the front and back body panels may be of elastic material. The elastic web material may be in the form of elastic nonwoven materials, nonwoven materials which per se are inelastic, but which have been elastified by means of elastic threads etc., elastic laminates composed of external layers of fibrous material and a middle elastic film layer.

The front and back panels 13 and 14 are joined along longitudinal side edges so as to form side seams 19. The front and back panels 13 and 14 can either be joined with the inner coversheets 17 of either the front or back panel facing the outer coversheet 18 of the opposite panel. In such case the side seam will be in the same plane as the adjacent portions of the front and back panels facing inwards in the side seams, as is shown in FIG. 5. Alternatively they are joined with the inner coversheets of the front and back panels facing inwards, wherein the side seam 19 will protrude from the plane of the front and back panels.

The front and back panels 13 and 14 are joined along the side seams 19 by a bonding pattern 4 according to an embodiment of the disclosure, comprising a main central bonding pattern 8 and two edge bonding patterns 9.

An elastic waistband 20 is secured to the front and back panels 13 and 14 along the waist opening. In its most common form the elastic waistband 20 comprises a substantially nonelastic nonwoven material that is elasticized by elongate elastic members 21, such as elastic threads or bands, contractably affixed between material layers, such as nonwoven materials. Alternatively the elastic waistband comprises an elastic nonwoven or an elastic film-nonwoven laminate. The elastic waistband 20 is joined to the front and back panels 13 and 14 by a bonding pattern 4 according to an embodiment of the disclosure.

The leg openings 12 are also elasticized, said elastification is usually accomplished by a plurality of elastic members 12a, such as elastic threads, which are contractably affixed between the outer and inner coversheets.

FIGS. 6 and 7 of the drawings show an embodiment of an absorbent garment in the form of a diaper or incontinence guard 22 comprising a first body panel 23 and a second body panel 24, and a crotch portion 25 there between. An absorbent core 26 is disposed in the crotch portion 25 and extends into the first and second body panels 23 and 24. The absorbent core 26 is disposed between an inner coversheet 27 and an outer coversheet 28.

The inner and outer coversheets and the absorbent core may be of the materials mentioned above with respect to the pant diaper. The garment has a longitudinal direction y and a transverse direction x.

A pair of belt members 29 are attached to the waist portion of second body panel 24 and are intended to be wrapped around the waist of the wearer of the garment and fastened together by means of first fastening means 30, for example a mechanical fastener, especially a hook fastener of a hook-and-loop fastening means. The external surface of the opposite belt member, especially if this comprises a fibrous nonwoven, may function as a loop member.

A "hook-and-loop fastener" refers to complementary fastening means having a "hook" portion and a "loop" portion and which are refastenable. The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials. Hook-and-loop fasteners are for example available from Velcro, USA.

Alternatively the first fastening means 30 is an adhesive fastening means such as a tape tab, wherein the external surface of opposite belt member 29 may be of a material to which the tape can adhere, as for example described in WO 01/00129.

The width of the belt members 29 should be from 5 to 20 cm, preferably from 7 to 15 cm. The belt members 29 are preferably made from a laminate of a carrier material, which forms the external surface of the belt, and a soft nonwoven, which forms the inside of the belt which is intended to be in direct contact with the skin of the user.

A suitable nonwoven material can be a spunbond material of e.g. polypropylene or polyethylene fibres. Conjugate fibres may also be used. Another suitable nonwoven material is formed from a carded thermobonded material of e.g. polypropylene, polyester or conjugate fibres.

The carrier material should be adapted to function as a reception surface for the fastening means 30. In case the fastening means is a hook fastener a nonwoven material may be used as a carrier material. In case the fastening means 30 is a tape tab, a plastic film is suitable as carrier material.

The first body panel 23, which normally is the front body panel, is then passed between the legs of the wearer and fastened to the outside of the belt members 29 by means of second fastening means 31 provided at the lateral edges of the waist portion of the front panel 23. These second fastening means 31 are mechanical fasteners, such as hook fasteners, or adhesive tape fasteners.

Each belt member 29 comprises at its proximal end adjacent the first body panel 24, an elastic region 29a. Said elastic region 29a may be in the form of an elastic web material such as an elastic film, an elastic nonwoven, an elastic laminate or the like. The elastic laminate may be a laminate between two or more nonwoven layers, two or more film layers or a combination of film and nonwoven layers.

Examples of elastic laminates suitable for forming said elastic regions 29a are any elastic laminate known in the art.

One group of elastic laminates are so called "stretch-bonded" laminates, in which the elastic layer is stretched in at least one direction before laminating it with one or more inelastic layers. After the tension is removed from the elastic layer it can freely retract to its untensioned state, and the inelastic layer(s) laminated thereto become gathered, giving a three-dimensional puckering.

Another group of elastic laminates are so called "neck bonded" laminates, which refer laminates in which an elastic material is bonded to a non-elastic material while the non-elastic member is extended under conditions reducing its width or necked. "Neck bonded laminate" refers to a composite material having at least two layers in which one layer is a necked, non-elastic layer and the other layer is an elastic layer. The layers are joined together when the non-elastic layer is in an extended condition.

A further group of elastic laminates are disclosed in for example WO/047488, in which inelastic nonwoven layers are laminated to an elastic film layer, and the laminate is stretched above the point of failure of the nonwoven materials, so that the inelastic layers break.

Examples of elastic laminates are described in EP-B-0 646 062, WO 98/29251, WO 03/000165 and U.S. Pat. No. 5,226, 992. Examples of commercially available elastic laminates are Fabriflex 306 from Tredegar and PK 6358 from Nordenia.

The elastic regions 29a preferably have an elasticity of at least 30% as measured in the elasticity test as described below.

Alternatively the elastic regions 29a comprises one or more elastic threads or strips contractably affixed between web material layers.

In an alternative embodiment only one belt member 29 is provided with an elastic region 29a.

A waist elastic member 32 extends in transverse direction, x, along at least part of the waist portion of each body panel 23 and 24. The waist elastic member may be an elastic web material such as an elastic laminate, an elastic film or the like contractably attached between the inner and outer coversheets, to the external side of the outer coversheet or to the wearer facing side of the inner coversheet. Alternatively it comprises two or more elastic threads or strips contractably affixed between the outer and inner coversheets.

The leg openings are also elasticized, said elastification is usually accomplished by a plurality of elastic members 33, such as elastic threads, which are contractably affixed between the outer and inner coversheets.

The elastic region 29a is bonded to the respective belt member 10 and/or to the first body panel 24 side edge by a bonding pattern 4 according to an embodiment of the disclosure.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05N |

The sample is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the web material should have a permanent relaxation after elongation of less than 10% after being exerted to an elongation of 30% in the tensile tester above. An elongation of 30% means an elongation to a length that is 30% longer than the initial length of the sample.

Although only a few exemplary embodiments of bonding patterns and applications for the bonding pattern according to the disclosure have been described in detail above, those skilled in the art will readily understand that many modifications are possible both with respect to the configuration of the bonding pattern and applications therefore.

The invention should not be considered as limited by the above description; rather the scope and limitations of the invention are defined by the enclosed granted claims and equivalents there.

The invention claimed is:

1. A seam joining together at least first and second web materials, at least one of which comprising heat fusible material, the first web material having a side edge overlapping with a side edge of the second web material, wherein an overlapped portion is formed where said web materials overlap, said web materials in said overlapped portion being bonded together in a bonding pattern extending over at least a part of the overlapped portion to form said seam, said overlapped portion having a longitudinal and transverse direction and a pair of longitudinal side edges defined by said overlapping side edges of the web materials, wherein said bonding pattern comprises a main bonding pattern extending in the longitudinal direction along at least a part of the overlapped portion, and at least one edge bonding pattern extending in the longitudinal direction along and adjacent at least a part of at least one of said side edges, wherein said main bonding pattern is defined in the longitudinal direction by an outer limiting margin and said edge bonding pattern is defined in the longitudinal direction by an inner limiting margin, wherein the distance between said outer and said inner limiting margin is at least 1.5 mm such that the main bonding pattern is spaced from the edge bonding pattern by at least 1.5 mm, and the bonded area of said edge bonding pattern(s) occupies no more than 30% of the total bonded area of the main bonding pattern plus the bonded area of the edge bonding pattern(s).

2. A seam as claimed in claim 1, wherein said edge bonding pattern occupies at least 5% of the total bonding area occupied by the combined main bonding pattern and edge bonding pattern.

3. A seam as claimed in claim 1 wherein said edge bonding pattern occupying no more than 25% of the total bonding area occupied by the combined main bonding pattern and edge bonding pattern.

4. A seam as claimed in claim 1, wherein said edge bonding pattern is in the form of a plurality of small bonding sites each having an area of no more than 4 $mm^2$.

5. A seam as claimed in claim 1, wherein said bonding pattern comprises two edge bonding patterns, one on each side of the main bonding pattern.

6. A seam as claimed in claim 5, wherein the distance between the inner limiting margins of the two edge bonding patterns is between 25 and 95% of the width of the seam overlapped portion in transverse direction.

7. A seam as claimed in claim 1, wherein the width of the overlapped portion in transverse direction is between 8 and 30 mm.

8. A seam as claimed in claim 1, wherein said main bonding pattern has a bonding density of between 10 and 80% of the area circumscribed by the bonding pattern including the non-bonded area between bonding sites.

9. A seam as claimed in claim 1, wherein said edge bonding pattern has a bonding density of at least 2% and no more than 60% of the area circumscribed by the bonding pattern including the non-bonded area between bonding sites.

10. A seam as claimed in claim 1, wherein said web materials have basis weight between 25 and 130 $g/m^2$.

11. A seam as claimed in claim 1, wherein at least one of the web materials is an elastic material.

12. A seam as claimed in claim 1, wherein the seam is located in the same plane as the web materials that are joined together.

13. A personal care absorbent article comprising an absorbent structure and first and second web materials comprising heat fusible material joined together at a seam formed by a bonding pattern as claimed in claim 1.

14. A personal care absorbent article as claimed in claim 13, wherein said personal care absorbent article is a pant-like garment comprising a first body panel, a second body panel and a crotch portion there between, said first and second body panels being joined together in an overlapped manner to form side seams joined by the bonding pattern.

15. A personal care absorbent article as claimed in claim 13, wherein said personal care absorbent article is a pant-like garment comprising a first body panel, a second body panel and a crotch portion there between, said first and second body panels being joined together to form side seams and further being provided with an elastic waistband, said waistband being joined to the first and/or second body panels in an overlapped manner to form said seam defined by the bonding pattern.

16. A personal care absorbent article as claimed in claim 13, wherein said personal care absorbent article is an absorbent garment comprising a first body panel, a second body panel and a crotch portion there between, each of said first and second body panels having a waist portion, said garment further being provided with opposed laterally extending belt members attached to the waist portion of the second body panel and being adapted to be wrapped around the waist of the wearer of the garment and fastened together by first fasteners, the first body panel at its waist portion being provided with second fasteners adapted to be fastened to the belt members, in such a way that the garment will assume a pant-like shape, at least one of the belt members comprises an elastic region located at the proximal end of said belt member adjacent the waist portion of the second body panel, said elastic region being joined to the rest of the respective belt member and/or to the second body panel in an overlapped manner to form said seam defined by the bonding pattern.

* * * * *